US005750407A

United States Patent [19]

Becker

[11] Patent Number: 5,750,407
[45] Date of Patent: May 12, 1998

[54] TEST METHOD FOR HYDRAULIC FLUIDS BASED ON GLYCOLS AND GLYCOL BORATES WITH RESPECT TO PRECIPITATION TENDENCY

[75] Inventor: Wilfried Becker, Neuötting, Germany

[73] Assignee: Hoechst Aktiengesellschaft, Frankfurt, Germany

[21] Appl. No.: 766,401

[22] Filed: Dec. 12, 1996

[30] Foreign Application Priority Data

Dec. 15, 1995 [DE] Germany ............... 195 46 856.2

[51] Int. Cl.⁶ ..................... G01N 33/00; G01N 31/02
[52] U.S. Cl. ................ 436/131; 436/164; 436/179; 436/183
[58] Field of Search ................... 436/131, 127, 436/164, 179, 183

[56] References Cited

U.S. PATENT DOCUMENTS

| 3,324,036 | 6/1967 | Shiffler | 252/75 |
|---|---|---|---|
| 3,711,411 | 1/1973 | Sawyer et al. | 252/78 |
| 3,859,321 | 1/1975 | Traver | 252/78.3 |
| 3,926,821 | 12/1975 | LeSuer | 252/46.7 |
| 3,931,342 | 1/1976 | Sheng | 260/637 R |
| 3,972,822 | 8/1976 | Sato et al. | 252/78.1 |
| 3,974,080 | 8/1976 | Coffman et al. | 252/78.3 |
| 4,051,053 | 9/1977 | Elliott et al. | 252/78.3 |
| 4,056,546 | 11/1977 | Brown, Jr. | 260/448.8 |
| 4,173,542 | 11/1979 | Sato et al. | 252/78.1 |
| 4,192,759 | 3/1980 | Hamanaka | 252/78.1 |
| 4,298,488 | 11/1981 | Tanizaki et al. | 252/78.1 |
| 4,340,495 | 7/1982 | Brown, Jr. | 252/78.3 |

FOREIGN PATENT DOCUMENTS

B-65470  11/1995  Ireland.

*Primary Examiner*—Arlen Soderquist
*Attorney, Agent, or Firm*—Connolly and Hutz

[57] ABSTRACT

The method described comprises the steps of, firstly, a water content of from 3 to 20 wt %, based on the water-containing fluid, being set in the hydraulic fluid to be tested, followed by the water-containing fluid being mixed with at least 1 part by volume of tetrahydrofuran or monoethylene glycol dimethyl ether per part by volume of water-containing fluid, whereupon the formation or nonformation of a precipitate is ascertained.

5 Claims, No Drawings

TEST METHOD FOR HYDRAULIC FLUIDS BASED ON GLYCOLS AND GLYCOL BORATES WITH RESPECT TO PRECIPITATION TENDENCY

DESCRIPTION

The invention relates to a method for testing hydraulic fluids, particularly brake fluids, based on glycols and glycol borates and containing amine compounds as additives with respect to precipitation tendency.

Such hydraulic fluids have been known for a long time, for example from U.S. Pat. No. 3,972,822, DE-A-40 13 243 (IE-B-65470) and U.S. Pat. No. 3,711,411. These publications further disclose that some of these fluids, particularly in conjunction with water being present, give rise to precipitates, cf. U.S. Pat. No. 3 711 411, first page. Precipitates, whether crystalline or not, and sometimes even if they are mere hazes, may lead to serious consequences, particularly in brake fluids, for example by the brake fluid line becoming blocked, with consequent loss of the braking effect. It would therefore be desirable to have a test which provides the possibility to predict whether the brake fluid does or does not tend to form precipitates.

We have found that, in particular, the hydraulic fluids based on glycols and their borates to suffer from a precipitation tendency, are those which contain amines as additives (corrosion inhibitors, pH stabilizers and the like), and that, in this context, precipitates occur primarily in those cases, where a specific water content is present.

The method according to the invention comprises the steps of, firstly, a water content of from 3 to 20 wt %, preferably from 4 to 10 wt %, based on the water-containing fluid, being set in the hydraulic fluid to be tested, followed by the water-containing fluid being mixed with at least 1 part by volume of tetrahydrofuran or monoethylene glycol dimethyl ether, preferably with at least 2 parts by volume and particularly with 2 to 10 parts by volume of tetrahydrofuran or monoethylene glycol dimethyl ether per part by volume of water-containing fluid, whereupon the formation or non-formation of a precipitate is ascertained.

The minimum amount of tetrahydrofuran or monoethylene glycol dimethyl ether (hereinafter also referred to as precipitant) per part by volume of the hydraulic fluid to be tested and having the specified water content is, according to the invention, at least 1 part by volume and preferably at least 2 parts by volume. Although the upper limit of the amount of precipitant is noncritical and can be chosen to be arbitrarily high, this too will be subject to a limit on grounds of expediency. The particularly preferred amount of precipitant is therefore from approximately 2 to 10 parts by volume.

According to a preferred test method according to the invention, 1 part by volume of the fluid to be tested, having the water content, set according to the invention, of from 3 to 20 wt %, preferably from 4 to 10 wt %, is accordingly mixed with from 2 to 10 parts by volume of precipitant. Preferably, a chemically pure precipitant is used, i.e. a tetrahydrofuran and a monoethylene glycol dimethyl ether having a purity of at least 98 to 99 wt %. Of the two precipitants, preference is given to tetrahydrofuran. The test method according to the invention is generally carried out at atmospheric pressure and room temperature, i.e. the components to be mixed are generally at from 15 to 30° C. The process of mixing the hydraulic fluid to be tested with the precipitant can, for example, be carried out in a test tube or beaker with agitation or stirring. As a rule, clouding or precipitation appears immediately after mixing, if the fluid in question tends to form precipitates. Occasionally, these phenomena may not appear until the mixture has been allowed to stand for about one to three weeks at room temperature. Otherwise the hydraulic fluid is one which does not tend to form precipitates.

The hydraulic fluids in question and, in particular, brake fluids preferably comprise essentially from 40 to 95 wt %, preferably from 60 to 80 wt %, of at least one glycol borate, from 0.05 to 10 wt %, preferably from 0.1 to 5 wt %, of at least one amine compound from the group consisting of alkanolamines which may or may not be alkoxylated, alkylamines and benzylamine or cyclohexylamine, and further comprise glycol compounds from the group consisting of alkylene glycols and oxalkylene glycols and their mono- and dialkyl ethers to make up 100 wt %, monoethylene glycol dimethyl ether being excluded. The customary glycol borates (i.e. reaction products from essentially glycols and/or glycol monoalkyl ethers and boric acid) individually, and likewise the glycol compounds and amine compounds are described in detail in the publications mentioned at the outset, which are incorporated herein by reference, especially DE-A-40 13 243.

The test method according to the invention has a number of advantages. It provides reliable information about hydraulic fluids with respect to precipitation tendency when the said water content is present. It can be carried out simply and inexpensively. The novel test method can be used for hydraulic fluids which have been used for long or short periods, which have been stored for long or short periods, or which have been freshly prepared, particularly brake fluids.

The invention will now be explained in more detail by way of some examples.

EXAMPLE 1

| | |
|---|---|
| 82.0% | of boric acid ester (formed from 3 mol of triethylene glycol monomethyl ether and 1 mol of boric acid) |
| 13.0% | of triethylene glycol monomethyl ether |
| 2.0% | of triethylene glycol dimethyl ether |
| 3.0% | of diisopropanolamine |

This brake fluid (having a water content of <0.1 wt %) was set to a water content of 8 wt %. 2 ml each of this water-containing brake fluid were mixed with 5 and 9 ml, respectively, of tetrahydrofuran. In both cases clouding was observed immediately, followed by the formation of a precipitate.

EXAMPLE 2

| | |
|---|---|
| 82.0% | of boric acid ester (as for Example 1) |
| 11.5% | of triethylene glycol monomethyl ether |
| 2.0% | of triethylene glycol dimethyl ether |
| 4.5% | of tributylamine |

The same procedure was followed as in Example 1. In neither case did clouding or the formation of a precipitate occur, even after a week's storage.

EXAMPLE 3

| | |
|---|---|
| 52.0% | of boric acid ester (formed from 2 mol of triethylene glycol monomethyl ether, 0.9 mol of diethylene glycol and 1 mol of boric acid) |
| 36.0% | of triethylene glycol monomethyl ether |
| 7.0% | of tetraethylene glycol monomethyl ether |
| 2.0% | of triethylene glycol dimethyl ether |
| 3.0% | of diisopropanolamine |

The same procedure was followed as in Example 1. In neither case did clouding or the formation of a precipitate occur, even after a week's storage.

Example 4

| | |
|---|---|
| 82.0% | of boric acid ester (as for Example 1) |
| 13.6% | of triethylene glycol monomethyl ether |
| 2.0% | of triethylene glycol dimethyl ether |
| 2.4% | of diethanolamine |

The same procedure was followed as in Example 1. In both cases clouding was observed immediately, followed by the formation of a precipitate.

Example 5

| | |
|---|---|
| 35.0% | of boric acid ester (as for Example 3) |
| 15.0% | of triethylene glycol monomethyl ether |
| 31.0% | of tetraethylene glycol monomethyl ether |
| 13.0% | of triethylene glycol monobutyl ether |
| 3.0% | of triethylene glycol dimethyl ether |
| 3.0% | of diisopropanolamine |

The same procedure was followed as in Example 1. In neither case did clouding or the formation of a precipitate occur, even after a week's storage.

Example 6

| | |
|---|---|
| 74.0% | of boric acid ester (as for Example 1) |
| 24.5% | of triethylene glycol monomethyl ether |
| 1.5% | of monoethanolamine |

The same procedure was followed as in Example 1. In both cases clouding was observed immediately, followed by the formation of a precipitate.

Example 7

| | |
|---|---|
| 82.0% | of boric acid ester (as for Example 1) |
| 11.5% | of triethylene glycol monomethyl ether |
| 2.0% | of triethylene glycol dimethyl ether |
| 4.5% | of cyclohexylamine |

The same procedure was followed as in Example 1. In neither case did clouding or the formation of a precipitate occur, even after a week's storage.

Example 8

| | |
|---|---|
| 82.0% | of boric acid ester (as for Example 1) |
| 13.0% | of triethylene glycol monomethyl ether |
| 2.0% | of triethylene glycol dimethyl ether |
| 3.0% | of diisopropanolamine |

The same procedure was followed as in Example 1. The precipitant used was monoethylene glycol dimethyl ether instead of tetrahydrofuran. In both cases clouding was observed immediately, followed by the formation of a precipitate.

Example 9

| | |
|---|---|
| 82.0% | of boric acid ester (as for Example 1) |
| 10.9% | of triethylene glycol monomethyl ether |
| 2.0% | of triethylene glycol dimethyl ether |
| 5.1% | of caprylamine + 2 EO |

The same procedure was followed as in Example 1. The precipitant used was monoethylene glycol dimethyl ether instead of tetrahydrofuran. In neither case did clouding or the formation of a precipitate occur, even after a week's storage.

I claim:

1. A method for testing precipitation tendency of hydraulic fluids based on glycols and glycol borates and containing amine compounds as additives, comprising the steps of adding water to a hydraulic fluid sample to form a water-containing fluid having a water content of from 3 to 20 weight percent, mixing the water-containing fluid with at least one part by volume of tetrahydrofuran or monoethylene glycol dimethyl ether per volume of water-containing fluid, and determining if a precipitate forms.

2. The method as claimed in claim 1, wherein the water content of the water-containing fluid is from 4 to 10 weight percent.

3. The method as claimed in claim 1 wherein the water-containing fluid is mixed with at least two parts by volume of tetrahydrofuran or monoethylene glycol dimethyl ether per volume of water-containing fluid.

4. The method as claimed in claim 1 wherein the water-containing fluid is mixed with from 2 to 10 parts by volume of tetrahydrofuran or monoethylene glycol dimethyl ether per volume of water-containing fluid.

5. The method as claimed in claim 1 wherein the water content of the water-containing fluid is from 4 to 10 weight percent, and the water-containing fluid is mixed with from 2 to 10 parts by volume of tetrahydrofuran or monoethylene glycol dimethyl ether per volume of water-containing fluid.

* * * * *